United States Patent
Kim et al.

(10) Patent No.: US 12,404,230 B2
(45) Date of Patent: Sep. 2, 2025

(54) METHOD FOR PREPARING A RECYCLED MATERIAL USING WASTE COPOLYESTER AND RECYCLED MATERIAL COMPOSITION

(71) Applicant: SK CHEMICALS CO., LTD., Seongnam-si (KR)

(72) Inventors: Ji-Hun Kim, Seongnam-si (KR); Kwang-Woo Park, Seongnam-si (KR); Joong Ki Lee, Seongnam-si (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 18/696,668

(22) PCT Filed: Dec. 7, 2023

(86) PCT No.: PCT/KR2023/020045
§ 371 (c)(1),
(2) Date: Mar. 28, 2024

(87) PCT Pub. No.: WO2024/154943
PCT Pub. Date: Jul. 25, 2024

(65) Prior Publication Data
US 2025/0034075 A1    Jan. 30, 2025

(30) Foreign Application Priority Data
Jan. 20, 2023   (KR) ................ 10-2023-0009078

(51) Int. Cl.
C07C 67/54    (2006.01)
C07C 67/02    (2006.01)
(Continued)

(52) U.S. Cl.
CPC ............ *C07C 67/54* (2013.01); *C07C 67/02* (2013.01); *C07C 69/82* (2013.01); *C08J 11/24* (2013.01); *C08J 2367/02* (2013.01)

(58) Field of Classification Search
CPC ......... C07C 69/82; C07C 67/02; C07C 67/54; C08J 11/24
See application file for complete search history.

(56) References Cited

U.S. PATENT DOCUMENTS

| 9,127,136 B1 * | 9/2015 | Bell | C07C 67/56 |
| 2022/0169786 A1 * | 6/2022 | Takao | C08G 63/183 |
| 2024/0158568 A1 * | 5/2024 | Hwang | C08G 63/183 |

FOREIGN PATENT DOCUMENTS

| JP | 2002-514661 A | 5/2002 |
| JP | 2002-167468 A | 6/2002 |

(Continued)

OTHER PUBLICATIONS

JP 2005298354 (A), IS KK, Method for recovering ester monomer from polyester film, English translation, 21 pages (Year: 2005).*
(Continued)

*Primary Examiner* — Yate' K Cutliff
(74) *Attorney, Agent, or Firm* — Sughrue Mion, PLLC

(57) ABSTRACT

A method for preparing a recycled raw material uses a waste copolyester. The method for preparing a recycled raw material includes (1) depolymerizing a waste copolyester to obtain a first reactant; (2) removing impurities present in the first reactant to obtain a second reactant; (3) distilling the second reactant to obtain a third reactant containing crude recycled bis-2-hydroxyethyl terephthalate and a fourth reactant containing a recycled diol-ester; and (4) mixing the third reactant with an aqueous solvent and recrystallizing it to obtain a fifth reactant containing recycled bis-2-hydroxyethyl terephthalate and a filtrate.

19 Claims, 1 Drawing Sheet

(51) Int. Cl.
*C07C 69/82* (2006.01)
*C08J 11/24* (2006.01)

(56) References Cited

FOREIGN PATENT DOCUMENTS

| | | | | | |
|---|---|---|---|---|---|
| JP | 2005298354 | A | * | 10/2005 | ............ Y02W 30/62 |
| JP | 2009173554 | A | * | 8/2009 | ............ Y02W 30/62 |
| KR | 10-2022-0138819 | A | | 10/2022 | |
| KR | 10-2452871 | B1 | | 10/2022 | |
| WO | 2022/211581 | A1 | | 10/2022 | |
| WO | WO-2023163481 | A1 | * | 8/2023 | ............ C07C 67/54 |
| WO | WO-2023219335 | A1 | * | 11/2023 | ............ C07C 69/82 |
| WO | WO-2023249327 | A1 | * | 12/2023 | ............ C07C 67/62 |

OTHER PUBLICATIONS

JP 2009173554 (A), Teijin Fibers LTD, Method for recovering dimethyl terephthalate having iimproved hue from PET bottle waste, English translation, 11 pages (Year: 2009).*
WO 2023163481 (A!), Kim, J-H, et al., Method for preparing recycled bis(2-hydroxyethyl) terephthalate through multi-step depolymerization, English translation, 25 pages (Year: 2023).*
WO 2023219335 (A1), Park, J-Y, et al., Method for producing polyester resin an fiber comprising regenerated bis(2-hydrosyethyl) terephthalate, English translation, 37 pages (Year: 2023).*
WO 2023249327, Kim, H-N. et al., Method for storing recycled bis(2-hydroxyethyl) terephthalate and method for preparing polyester resin, English translation, 36 pages (Year: 2023).*
International Search Report for PCT/KR2023/020045 dated Mar. 11, 2024.

* cited by examiner

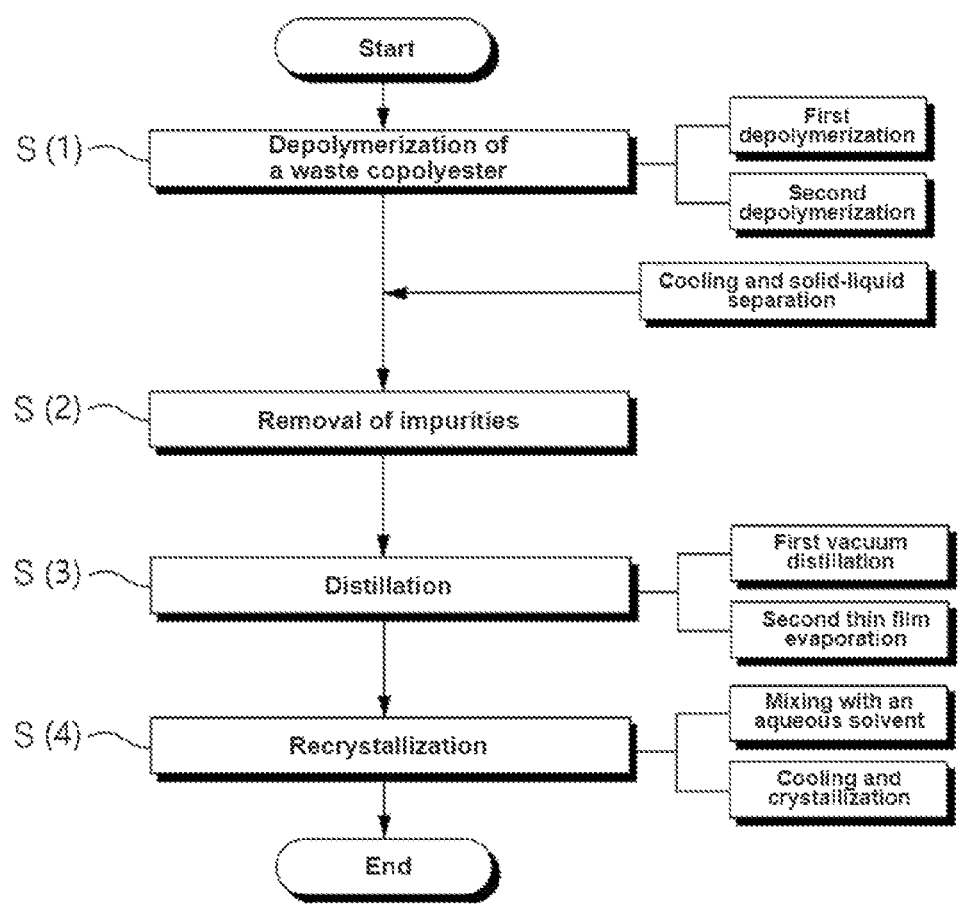

METHOD FOR PREPARING A RECYCLED MATERIAL USING WASTE COPOLYESTER AND RECYCLED MATERIAL COMPOSITION

CROSS REFERENCE TO RELATED APPLICATIONS

This application is a National Stage of International Application No. PCT/KR2023/020045 filed Dec. 7, 2023, claiming priority based on Korean Patent Application No. 10-2023-0009078 filed Jan. 20, 2023.

TECHNICAL FIELD

The present invention relates to a method for preparing various types of recycled raw materials with high efficiency using a waste copolyester and to a recycled raw material composition obtained from the waste copolyester.

BACKGROUND ART

Polyester, among polymers commonly used in modern life, is widely used as a material for containers for beverages and food, various packaging films, interior and exterior materials such as panels, shelves, and partitions, and the like by virtue of its excellent mechanical strength, thermal resistance, transparency, and gas barrier properties. As a result, waste of plastics such as polyester is generated globally at an unmanageable level every year. Recently, countries around the world have prepared regulations and plans for recycling waste plastic resources, including waste polyester.

Although physical recycling methods or chemical recycling methods are used as methods of recycling a waste polyester, physical recycling methods cannot guarantee purity and, therefore, are not widely used. Meanwhile, in chemical recycling methods, the ester bond of a waste polyester is severed to depolymerize it. Reactions such as glycolysis, hydrolysis, methanolysis, and aminolysis are used. Glycolysis among them is to decompose a waste polyester by adding a glycol such as ethylene glycol or diethylene glycol at high temperatures. A reaction product mainly containing bis-2-hydroxyethyl terephthalate (BHET) is obtained.

However, there is a significant amount of waste polyester that is actually discarded in the form of copolymers as well as homopolymers. When a waste polyester in the form of copolymers is depolymerized by the above chemical recycling methods, there are limitations in recycling various types of raw materials (e.g., comonomers, oligomers, or the like).

PRIOR ART DOCUMENT

Patent Document (Patent Document 1) Korean Laid-open Patent Publication No. 2022-0138819

DISCLOSURE OF INVENTION

Technical Problem

A reaction result (product) obtained by the depolymerization of a waste copolyester comprises diethylene glycol, oligomers such as diethylene glycol-esters, and comonomers used for the preparation of copolyesters, in addition to bis-2-hydroxyethyl terephthalate (BHET).

Diethylene glycol and diethylene glycol-esters are side reactants that are regarded as impurities. Their presence deteriorates the purity and color of the bis-2-hydroxyethyl terephthalate (BHET) and, therefore, deteriorates the physical properties of recycled polyester when the recycled polyester is prepared using bis-2-hydroxyethyl terephthalate (BHET).

Meanwhile, since the comonomers can be used as a recycled raw material together with bis-2-hydroxyethyl terephthalate (BHET), it is necessary to recycle them efficiently.

Accordingly, the present inventors have conducted various studies with a purpose of developing a technology that can increase the recycling rate of the comonomers while minimizing the production (residual) of side reactants such as diethylene glycol and diethylene glycol-esters when a waste copolyester is depolymerized. As a result, it has been discovered that the above purpose could be achieved by analyzing the substances produced during the depolymerization process, identifying the physical and chemical behavior of each substance, and separating each substance accordingly.

Accordingly, an object of the present invention is to provide a method for preparing a recycled raw material that can efficiently produce various kinds of recycled raw materials by using a waste copolyester, while increasing the recycling rate of the comonomers and minimizing the production of the side reactants.

In addition, another object of the present invention is to provide a recycled raw material composition obtained from a waste copolyester.

Solution to Problem

In order to accomplish the above object, the present invention provides a method for preparing a recycled raw material that comprises (1) depolymerizing a waste copolyester to obtain a first reactant; (2) removing impurities present in the first reactant to obtain a second reactant; (3) distilling the second reactant to obtain a third reactant comprising crude recycled bis-2-hydroxyethyl terephthalate and a fourth reactant comprising a recycled diol-ester; and (4) mixing the third reactant with an aqueous solvent and recrystallizing it to obtain a fifth reactant comprising recycled bis-2-hydroxyethyl terephthalate and a filtrate.

In addition, the present invention provides a recycled raw material composition that is obtained by the depolymerization of waste copolyester, wherein the peak area fraction of bis-2-hydroxyethyl terephthalate is 70% or less, and the peak area fraction of a diol-ester is 10% or more, when analyzed by high-performance liquid chromatography (HPLC).

In addition, the present invention provides a recycled raw material composition that is obtained by the depolymerization of waste copolyester, wherein the peak area fraction of bis-2-hydroxyethyl terephthalate is 95% or more, and the peak area fraction of a diol-ester is less than 1.5%, when analyzed by high-performance liquid chromatography (HPLC).

Advantageous Effects of Invention

According to the present invention, since a waste copolyester is depolymerized and subjected to thin film evaporation and recrystallization steps to prepare a recycled raw material, it is possible to efficiently prepare various kinds of recycled raw materials, along with recycled bis-2-hydroxyethyl terephthalate, while minimizing the production (residual) of diethylene glycol and diethylene glycol-esters regarded as impurities.

Accordingly, the present invention can solve the conventional problem of difficulty in recycling a waste copolyester. As a result, it is possible to impart high value to a waste copolyester as a recyclable resource.

In addition, since the present invention can produce various types of recycled raw materials with high purity (e.g., recycled bis-2-hydroxyethyl terephthalate, recycled cyclohexanedimethanol, recycled isosorbide, and the like), it is possible to provide recycled polyester (recycled copolyester) with excellent quality using the recycled raw materials, and products prepared using the same.

BRIEF DESCRIPTION OF DRAWING

The FIGURE is a flowchart showing the preparation process of a recycled raw material according to an embodiment of the present invention.

BEST MODE FOR CARRYING OUT THE INVENTION

Hereinafter, the present invention will be described in detail. The present invention herein is not limited to the disclosures given below, but it may be modified into various forms as long as the gist of the invention is not changed.

In the present specification, the term "comprising" is intended to specify a particular characteristic, region, step, process, element, and/or component. It does not exclude the presence or addition of any other characteristic, region, step, process, element and/or component, unless specifically stated to the contrary.

Throughout the present specification, the terms first, second, and the like are used for the purpose of distinguishing one element from another. But the components should not be limited by the terms.

All numbers and expressions related to the quantities of components, reaction conditions, and the like used herein are to be understood as being modified by the term "about" unless otherwise indicated.

Method for Preparing a Recycled Raw Material

The present invention provides a method for preparing a recycled raw material by analyzing the substances produced during the depolymerization of a waste copolyester and conducting a separation process appropriate for the physical and chemical behavior of each substance. Specifically, the method for preparing a recycled raw material according to the present invention comprises (1) depolymerizing a waste copolyester to obtain a first reactant; (2) removing impurities present in the first reactant to obtain a second reactant; (3) distilling the second reactant to obtain a third reactant comprising crude recycled bis-2-hydroxyethyl terephthalate and a fourth reactant comprising a recycled diol-ester; and (4) mixing the third reactant with an aqueous solvent and recrystallizing it to obtain a fifth reactant comprising recycled bis-2-hydroxyethyl terephthalate and a filtrate.

In the present invention, it is possible to efficiently separate comonomers such as cyclohexanedimethanol (CHDM), isosorbide (ISB), and the like, which are difficult to be separated from the reactant containing crude recycled bis-2-hydroxyethyl terephthalate obtained through the depolymerization of a waste copolyester. For example, the present invention is characterized in that cyclohexanedimethanol (CHDM), which competes for a transesterification reaction with a glycol-based compound (e.g., monoethylene glycol (MEG)) introduced into the depolymerization reaction of a waste copolyester, is separated and concentrated through thin film evaporation in the form of a cyclohexanedimethanol-ester (CHDM-ester) and recovered from the bottom of the reactor; and that isosorbide (ISB), which is inferior in a transesterification reaction to a glycol-based compound and cyclohexanedimethanol, is separated and concentrated through thin film evaporation, recovered from the upper section (top) of the reactor, and then recrystallized to be recovered in a single-molecular form.

Meanwhile, the recycled raw material in the present invention refers to a recycled monomer or a recycled oligomer derived from a waste copolyester. Specifically, it may comprise at least one selected from the group consisting of recycled bis-2-hydroxyethyl terephthalate (r-BHET), recycled cyclohexanedimethanol (r-CHDM), recycled tetramethylcyclobutanediol (r-TMCBD), recycled neopentyl glycol (r-NPG), recycled isosorbide (r-ISB), a recycled cyclohexanedimethanol-ester (r-CHDM-ester), a recycled tetramethylcyclobutanediol-ester (r-TMCBD-ester), a recycled neopentyl glycol-ester (r-NPG-ester), and a recycled isosorbide-ester (r-ISB-ester).

Hereinafter, each step of the method will be described in detail with reference to the FIGURE, as follows.

Step (1): Depolymerization

According to the present invention, step (1) is a step of depolymerizing a waste copolyester through a chemical recycling method (e.g., glycolysis reaction) to obtain a first reactant. Specifically, the first reactant may be obtained by conducting a chemical reaction to sever the polymer chain of the waste copolyester with a glycol-based compound.

The waste copolyester may be obtained by pretreating waste products discarded after they have been used by consumers. Specifically, the waste products may be beverage bottles, fabrics, films, cases, boxes, partitions, shelves, protective panels, packaging materials, building materials, and interior and exterior materials that comprise copolyester.

The copolyester contained in the various waste products may be obtained through a conventional (co) polymerization reaction of one or more commonly known acid components and one or more commonly known alcohol components. The acid component may specifically comprise at least one selected from the group consisting of terephthalic acid, isophthalic acid, dimethyl terephthalic acid, naphthalenedicarboxylic acid, orthophthalic acid, adipic acid, azelaic acid, sebacic acid, and decanedicarboxylic acid. The alcohol component may specifically comprise at least one selected from the group consisting of ethylene glycol, 1,3-propanediol, 1,2-octanediol, 1,3-octanediol, 2,3-butanediol, 1,3-butanediol, 1,4-butanediol, 1,5-pentanediol, neopentyl glycol, 2-butyl-2-ethyl-1,3-propanediol, 2,2-diethyl-1,5-pentanediol, 2,4-diethyl-1,5-pentanediol, 3-methyl-1,5-pentanediol, 1,1-dimethyl-1,5-pentanediol, 1,2-cyclohexanedimethanol, 1,3-cyclohexanedimethanol, 1,4-cyclohexanedimethanol, diethylene glycol, and 2,2,4,4-tetramethyl-1,3-cyclobutanediol.

The pretreatment may be carried out by removing other plastics, metals, and foreign substances mixed in the waste, washing it, and then crushing it through a crusher. As a result of the pretreatment, the waste copolyester may have a flake form. In addition, the waste copolyester may have a fine structure like a fiber.

Step (1) of depolymerizing a waste copolyester may comprise (1-1) first depolymerizing the waste copolyester to obtain a first-first reactant; and (1-2) second depolymerizing the first-first reactant to obtain the first reactant.

Step (1-1) may comprise a procedure of carrying out a chemical reaction for first severing the polymer chain of the waste copolyester with a first glycol-based compound to obtain the first-first reactant.

The first glycol-based compound used in the first depolymerization of step (1-1) is not particularly limited, but it may specifically comprise at least one selected from the group consisting of ethylene glycol (monoethylene glycol), propylene glycol, and diethylene glycol.

The feeding amount of the first glycol-based compound (the amount used in the first depolymerization) is not particularly limited, but it may specifically be 100 to 700 parts by weight, 100 to 600 parts by weight, 100 to 500 parts by weight, 200 to 500 parts by weight, 200 to 400 parts by weight, or 200 to 300 parts by weight, relative to 100 parts by weight of the waste copolyester. As the feeding amount of the first glycol-based compound is within the above range, the first depolymerization of the waste copolyester is carried out smoothly, and it is possible to prevent unreacted glycol-based compounds from remaining in excess.

The first depolymerization conditions in step (1-1) are not particularly limited, but it may specifically be carried out at 180 to 200° C. for 1 to 4 hours. More specifically, the first depolymerization temperature may be 180 to 195° C., 180 to 193° C., 180 to 190° C., 180 to 188° C., or 180 to 185° C. In addition, the first depolymerization time may be 1 to 4 hours, 1 to 3 hours, or 1 to 2 hours from the time the temperature required for the first depolymerization is reached. As the temperature and time of the first depolymerization are each within the above range, the first depolymerization of the waste copolyester is carried out smoothly, while minimizing the formation of side reactants such as diethylene glycol, diethylene glycol-esters, and the like.

The first depolymerization in step (1-1) may be carried out in the presence of a catalyst that activates the depolymerization reaction. The catalyst is not particularly limited as long as it is a commonly known catalyst, but it may specifically comprise a metal acetate, an anhydride thereof, or a hydride thereof. More specifically, the catalyst may be at least one acetate selected from the group consisting of zinc acetate, sodium acetate, cobalt acetate, and manganese acetate, a hydride thereof, or an anhydride thereof.

The feeding amount (the amount used) of the catalyst in step (1-1) is not particularly limited, but it may specifically be 0.01 to 5 parts by weight, 0.05 to 3 parts by weight, 0.1 to 2 parts, or 0.2 to 1 part by weight, relative to 100 parts by weight of the waste copolyester.

Step (1-2) may comprise a procedure of carrying out a chemical reaction for second severing the first-first reactant obtained in step (1-1) with a second glycol-based compound to obtain the first reactant.

The second glycol-based compound used in the second depolymerization of step (1-2) is not particularly limited, but it may specifically comprise at least one selected from the group consisting of ethylene glycol (monoethylene glycol), propylene glycol, and diethylene glycol. The second glycol-based compound may be derived from the first depolymerization procedure of step (1-1) or may be further added during the second depolymerization procedure of step (1-2).

The feeding amount of the second glycol-based compound (the amount used in the second depolymerization) is not particularly limited, but it may specifically be 100 to 700 parts by weight, 100 to 600 parts by weight, 100 to 500 parts by weight, 200 to 500 parts by weight, 200 to 400 parts by weight, or 200 to 300 parts by weight, relative to 100 parts by weight of the waste copolyester. As the feeding amount of the second glycol-based compound is within the above range, the second depolymerization of the first-first reactant is carried out smoothly, and it is possible to prevent unreacted glycol-based compounds from remaining in excess.

The second depolymerization conditions in step (1-2) are not particularly limited, but it may specifically be carried out at 150 to 170° C. for 1 to 4 hours. More specifically, the second depolymerization temperature may be 150 to 165° C., 150 to 163° C., 150 to 160° C., 150 to 158° C., or 150 to 155° C. In addition, the second depolymerization time may be 1 to 4 hours, 1 to 3 hours, or 1 to 2 hours from the time the temperature required for the second depolymerization is reached. As the temperature and time of the second depolymerization are each within the above range, the second depolymerization of the first-first reactant is carried out smoothly, while minimizing the formation of side reactants such as diethylene glycol, diethylene glycol-esters, and the like.

The second depolymerization in step (1-2) may be carried out in the presence of a catalyst that activates the depolymerization reaction. The catalyst may be derived from the first depolymerization procedure of step (1-1) or may be further added during the second depolymerization procedure of step (1-2). The description of the catalyst is the same as the description of the catalyst in step (1-1) above; thus, a detailed description is omitted.

As described above, the method for preparing a recycled raw material according to the present invention comprises the steps of first depolymerization and second depolymerization of a waste copolyester. As a result, it is possible to relatively minimize the production of side reactants such as diethylene glycol and diethylene glycol-esters as compared with the case where the first depolymerization alone is carried out by applying the same amount of raw materials and the same time.

Meanwhile, the method for preparing a recycled raw material according to the present invention may further comprise cooling the first reactant obtained in step (1) and subjecting it to solid-liquid separation before the impurity removal procedure in step (2) described below. Specifically, in the step of cooling and solid-liquid separation, the first reactant is cooled through a reduced pressure flash and then subjected to solid-liquid separation through a pressurized filtration procedure using a filter aid. As a result, the first reactant can be converted into a liquid reactant. As the step of cooling and solid-liquid separation is further carried out, solid foreign matters such as particulates and insoluble organic substances contained in the first reactant are removed, thereby increasing the yield and purity of the recycled raw material finally obtained.

The temperature at which the first reactant is cooled through the reduced pressure flash is not particularly limited, but it may specifically be 135° C. or lower, 130° C. or lower, 125° C. or lower, 120° C. or lower, or 115° C. or lower, and 100° C. or higher, 105° C. or higher, or 110° C. or higher (e.g., 100 to 135° C., 105 to 125° C., or 110 to 120° C.).

The pressure in the reduced pressure flash is not particularly limited, but it may specifically be 200 Torr or less, 150 Torr or less, 100 Torr or less, 50 Torr or less, or 30 Torr or less, and 5 Torr or more, 8 Torr or more, 10 Torr or more, or 15 Torr or more (e.g., 5 to 200 Torr, 10 to 100 Torr, or 15 to 50 Torr).

The filter aid used for the solid-liquid separation is not particularly limited as long as it is commonly known, but it may specifically comprise at least one selected from the group consisting of diatomaceous earth, perlite, and asbestos powder.

The feeding amount (the amount used) of the filter aid is not particularly limited, but it may specifically be 0.01 to 2 parts by weight, 0.05 to 2 parts by weight, 0.05 to 1 part by weight, or 0.1 to 1 part by weight, relative to 100 parts by weight of the first reactant.

Step (2): Removal of Impurities

According to the present invention, step (2) is a step of removing impurities present in the first reactant obtained in step (1) to obtain a second reactant. Here, if the first reactant has been further subjected to the step of cooling and solid-liquid separation, the first reactant is in the state of a liquid reactant from which solid impurities have been removed. The removal of impurities may be carried out for the liquid reactant.

The removal of impurities in step (2) may specifically be carried out through an ion-exchange resin. More specifically, the removal of impurities may be carried out by passing the first reactant (liquid reactant) through an ion exchange resin or adding an ion exchange resin to the first reactant (liquid reactant). As such an impurity removal step is carried out, ionic impurities (e.g., catalysts and metal foreign substances) contained in the first reactant may be removed to obtain a second reactant with high purity.

The ion-exchange resin used for removing impurities may be a cation-exchange resin, an anion-exchange resin, an amphoteric ion-exchange resin, a chelate resin, or the like, commonly known.

The cation-exchange resin may specifically comprise a strongly acidic cation-exchange resin having a sulfonic acid group (—SO$_3$H) or a weakly acidic cation-exchange resin having a carboxyl group (—COOH). The anion-exchange resin may comprise a strongly basic anion-exchange resin in the form of a quaternary ammonium salt or a weakly basic anion-exchange resin having a primary to tertiary amino group. The chelate resin may be a polymer resin having a reactive functional group such as acetate or phosphate that chelates metal ions such as sodium, copper, nickel, zinc, and manganese.

When the impurity removal is carried out by adding the ion-exchange resin to the first reactant, the feeding amount (the amount used) of the ion-exchange resin is not particularly limited, but it may be 1 times or more, 2 times or more, 3 times or more, or 5 times or more, and 20 times or less, 15 times or less, 10 times or less, or 8 times or less (e.g., 1 to 20 times, 2 to 15 times, 3 to 10 times, or 5 to 8 times) the weight of the catalyst used in the depolymerization of the step (1). In addition, the feeding amount (the amount used) of the ion-exchange resin may be 1 part by weight or more, 2 parts by weight or more, 3 parts by weight or more, or 5 parts by weight or more, and 50 parts by weight or less, 20 parts by weight or less, 15 parts by weight or less, 10 parts by weight or less, or 7 parts by weight or less (e.g., 1 to 50 parts by weight, 3 to 20 parts by weight, or 5 to 10 parts by weight), relative to 100 parts by weight of the waste copolyester of step (1).

Meanwhile, when the impurity removal is carried out by passing the first reactant to the ion-exchange resin, the ion-exchange resin may be in the form of particles having a predetermined size. Specifically, the impurity removal may be carried out by passing the first reactant through a column filled with ion-exchange resin particles having a particle size of 0.3 to 1.5 mm, 0.5 to 1.3 mm, or 0.7 to 1.0 mm.

Step (3): Distillation

According to the present invention, step (3) is a step of distilling the second reactant to obtain a third reactant comprising crude recycled bis-2-hydroxyethyl terephthalate and a fourth reactant comprising a recycled diol-ester. Step (3) may comprise (3-1) first distilling the second reactant to obtain a second-first reactant; and (3-2) second distilling the second-first reactant to obtain the third reactant comprising crude recycled bis-2-hydroxyethylterephthalate and the fourth reactant comprising a recycled diol-ester.

Step (3-1) may comprise a procedure of carrying out a first distillation of the second reactant through a commonly known distillation process to obtain the second-first reactant. Specifically, the first distillation may be carried out as vacuum distillation so that the unreacted glycol-based compounds contained in the second reactant can be efficiently removed. As a result, the second-first reactant in which the unreacted glycol-based compounds have been removed can be obtained.

A glass distillation apparatus or a rotary evaporator may be used for the first vacuum distillation in step (3-1).

The first vacuum distillation conditions of step (3-1) are not particularly limited, but it may specifically be carried out at 150° C. or lower under a pressure of 0.1 to 200 Torr. More specifically, the pressure of the first vacuum distillation may be 0.1 to 150 Torr, 0.2 to 100 Torr, 0.3 to 50 Torr, or 0.5 to 30 Torr. In addition, the temperature of the first vacuum distillation may be 90° C. or higher, 100° C. or higher, or 110° C. or higher, and 145° C. or lower, 140° C. or lower, or 135° C. or lower (e.g., 90 to 150° C., 100 to 145° C., or 120 to 135° C.).

The unreacted glycol-based compound removed through the first vacuum distillation can be recovered and reused in the depolymerization procedure of step (1), thereby increasing the economic efficiency of the depolymerization process.

Meanwhile, in the method for preparing a recycled raw material according to the present invention, step (3) may further comprise subjecting the second-first reactant obtained through the first vacuum distillation of step (3-1) to solid-liquid separation before the second distillation of step (3-2). Specifically, the solid-liquid separation may be carried out with a pressurized filter, an adsorbent (e.g., activated carbon), a centrifugal separator, a filter press, a belt press, or the like. As a result, insoluble foreign substances contained in the second-first reactant can be removed.

Step (3-2) may comprise a procedure of carrying out a second distillation of the second-first reactant through a commonly known distillation process to obtain the third reactant and the fourth reactant. Specifically, the secondary distillation may be carried out by thin film evaporation for efficient separation of crude recycled bis-2-hydroxyethyl terephthalate from recycled comonomers (e.g., recycled cyclohexanedimethanol, recycled isosorbide, and the like) and recycled diol-esters, contained in the second-first reactant. More specifically, the secondary distillation may be carried out by thin film evaporation using a thin film evaporator. As the thin film evaporation is carried out, a third reactant (distillate) containing crude recycled bis-2-hydroxyethyl terephthalate can be obtained from the top of the thin film evaporator, and a fourth reactant containing a recycled diol-ester (residue from which the distillate has been removed) can be obtained from the bottom of the thin film evaporator.

The recycled diol-ester contained in the fourth reactant may not be particularly limited as long as it is a compound having two hydroxy groups (OH) and an ester structure (C═O). Specifically, the recycled diol-ester may comprise at least one selected from the group consisting of a recycled cyclohexanedimethanol-ester (r-CHDM-ester), a recycled isosorbide-ester (r-ISB-ester), a recycled tetramethylcyclobutanediol-ester (r-TMCBD-ester), and a recycled neopentylglycol-ester (r-NPG-ester). Preferably, it may be recycled a cyclohexanedimethanol-ester (r-CHDM-ester). Here, examples of the recycled diol-ester may exclude (may not include) a diethylene glycol-ester (recycled diethylene glycol-ester) regarded as an impurity.

The recycled cyclohexanedimethanol-ester may specifically comprise at least one selected from the group consisting of 1-(2-hydroxyethyl) 4-[[4-(hydroxymethyl)cyclohexyl]methyl] terephthalate (CHDM-ester-1); 1,1'-[1,4-cyclohexanediylbis(methylene)] 4,4'-bis(2-hydroxyethyl) terephthalate (Dimer-2 and Dimer-3); and 1,4-benzenedicarboxylic acid, 1-[2-[[4-[(2-hydroxyethoxy)carbonyl]benzoyl]oxy]ethyl]-4-[2-[[4-[((hydroxymethyl)cyclohexyl] methoxy)carbonyl]benzoyl]oxy]ethyl] ester (Trimer-2).

The fourth reactant may further comprise a recycled comonomer in addition to the recycled diol-ester. The recycled comonomer may specifically comprise at least one selected from the group consisting of recycled cyclohexanedimethanol, recycled tetramethylcyclobutanediol, recycled neopentylglycol, and recycled isosorbide.

For example, the fourth reactant may comprise at least one selected from the group a recycled cyclohexanedimethanol-ester and consisting of recycled cyclohexanedimethanol.

Such recycled diol-esters and/or recycled comonomers can be recovered through an additional purification process of the fourth reactant.

Meanwhile, the recycled diol-esters and/or the recycled comonomers may be contained in the third reactant in addition to the fourth reactant. Since the description thereof is the same as described above, it is omitted.

The thin film evaporator for the second thin film evaporation in step (3-2) may comprise an evaporator, a wiper rotor, and a condenser.

The second thin film evaporation conditions of step (3-2) are not particularly limited, but it may be carried out at 180 to 235° C. under a pressure of 0.005 to 5 Torr. More specifically, the pressure of the second thin film evaporation may be 0.01 to 4 Torr, 0.05 to 3 Torr, or 0.07 to 1.5 Torr. In addition, the temperature of the second thin film evaporation (internal thin film temperature of the thin film evaporator) may be 185 to 230° C., 190 to 225° C., 195 to 220° C., or 200 to 215° C. As the temperature and pressure of the second thin film evaporation are each within the above range, it is possible to maximize the efficiency of separating the third reactant containing crude recycled bis-2-hydroxyethyl terephthalate and the fourth reactant containing a recycled diol-ester. In particular, the recovery concentration index (RCI) of a recycled diol-ester (e.g., recycled cyclohexanedimethanol-ester) described below can be controlled to the desired range to secure the required level of separation efficiency.

The third reactant obtained through step (3) may have a peak area fraction of bis-2-hydroxyethyl terephthalate of 90% or more, specifically, 90 to 99%, 90 to 98%, 90 to 97%, or 90 to 96%, when analyzed by high-performance liquid chromatography (HPLC). In addition, the third reactant may have a peak area fraction of a diol-ester (e.g., cyclohexanedimethanol-ester) of 4% or less, specifically, 0.5 to 4%, 0.8 to 3.5%, 1 to 3.2%, or 1.5 to 2.5%, when analyzed by high-performance liquid chromatography (HPLC).

In addition, the fourth reactant obtained through step (3) may have a peak area fraction of bis-2-hydroxyethyl terephthalate of 70% or less, specifically, 20 to 70%, 25 to 67%, 30 to 65%, or 40 to 50%, when analyzed by high-performance liquid chromatography (HPLC). In addition, the fourth reactant may have a peak area fraction of a diol-ester (e.g., cyclohexanedimethanol-ester) of 10% or more, specifically, 10 to 40%, 11 to 38%, 15 to 35%, or 20 to 30%, when analyzed by high-performance liquid chromatography (HPLC).

Meanwhile, in the method for preparing a recycled raw material according to the present invention, the recovery concentration index (RCI) according to the following Equation 1 may be 0.5 to 0.99. Specifically, the recovery concentration index (RCI) may be 0.55 to 0.99, 0.6 to 0.99, 0.65 to 0.99, 0.7 to 0.98, 0.75 to 0.98, or 0.8 to 0.97. The recovery concentration index refers to the partition coefficient of a recycled diol-ester (e.g., recycled cyclohexanedimethanol-ester (r-CHDM-ester)) separated according to the second thin film evaporation conditions of step (3-2). When the recovery concentration index is within the above range, it may mean that the separation of the third reactant and the fourth reactant is very well conducted.

$$RCI = CE_2/(CE_1 + CE_2) \qquad \text{[Equation 1]}$$

In Equation 1, $CE_1$ is the peak area fraction of the identified diol-ester (total peak area fraction of a diol-ester) when the third reactant is analyzed by high-performance liquid chromatography (HPLC), and $CE_2$ is the peak area fraction of the identified diol-ester (total peak area fraction of a diol-ester) when the fourth reactant is analyzed by high-performance liquid chromatography (HPLC).

Step (4): Recrystallization

According to the present invention, step (4) is a step of mixing the third reactant obtained in step (3) with an aqueous solvent and recrystallizing it to obtain a fifth reactant comprising recycled bis-2-hydroxyethyl terephthalate and a filtrate. Step (4) may comprise (4-1) mixing the third reactant with the aqueous solvent to obtain an aqueous solution; and (4-2) cooling and crystallizing the aqueous solution and subjecting it to solid-liquid separation to obtain the fifth reactant containing recycled bis-2-hydroxyethyl terephthalate (r-BHET) and the filtrate.

Step (4-1) may comprise a procedure of adding the aqueous solvent to the third reactant to mix and dissolve it to obtain an aqueous solution. The temperature at which the third reactant is dissolved is not particularly limited, but it may specifically be 50 to 90° C., 55 to 85° C., 60 to 80° C., or 65 to 75° C. As the dissolving temperature is within the above range, the yield of recycled bis-2-hydroxyethyl terephthalate (r-BHET) can be increased. Meanwhile, the aqueous solvent may specifically be water, distilled water, deionized water, or pure water.

Step (4-2) may comprise a procedure of cooling the aqueous solution to crystallize (recrystallize) and subjecting it to conventional solid-liquid separation to obtain the fifth reactant containing recycled bis-2-hydroxyethyl terephthalate (r-BHET) and the filtrate. The temperature at which the aqueous solution is cooled is not particularly limited, but it may specifically be 20 to 30° C., 22 to 28° C., or 24 to 26° C.

As the third reactant is converted into an aqueous solution through step (4-1), and the aqueous solution is cooled and recrystallized through step (4-2), it is possible to maximize the separation efficiency of recycled bis-2-hydroxyethylterephthalate (r-BHET) and comonomers (e.g., recycled isosorbide) while increasing the yield of recycled bis-2-hydroxyethylterephthalate (r-BHET).

The fifth reactant obtained through step (4) may have a peak area fraction of bis-2-hydroxyethyl terephthalate of 95% or more, specifically, 95 to 99.5%, 95.5 to 99%, 96 to 98%, or 97 to 98%, when analyzed by high-performance liquid chromatography (HPLC). In addition, the fifth reactant may have a peak area fraction of a diol-ester (e.g., cyclohexanedimethanol-ester) of less than 1.5%, specifically, 0.2 to 1.4%, 0.3 to 1.3%, 0.4 to 1.2%, or 0.5 to 1.1%, when analyzed by high-performance liquid chromatography (HPLC).

Meanwhile, in the method for preparing a recycled raw material according to the present invention, the total peak area fraction (PAT) of a diol-ester (e.g., cyclohexanedimethanol-ester) may be 0.1 to 70% when the fourth reactant of step (3) and the fifth reactant of step (4) are each analyzed by high-performance liquid chromatography (HPLC). Specifically, the total peak area fraction (PAT) according to the following Equation 2 may be 1 to 70%, 5 to 60%, 10 to 50%, or 15 to 45%.

$$PA_T = PA_1 + PA_2 \qquad \text{[Equation 2]}$$

in Equation 2, $PA_1$ is the peak area fraction of the identified diol-ester (e.g., cyclohexanedimethanol-ester) when the fourth reactant is analyzed by high-performance liquid chromatography (HPLC), and $PA_2$ is the peak area fraction of the identified diol-ester (e.g., cyclohexanedimethanol-ester) when the fifth reactant is analyzed by high-performance liquid chromatography (HPLC).

Meanwhile, the filtrate obtained through step (4) may comprise recycled isosorbide (r-ISB) in an amount of 0.1 to 30% by weight based on the total weight of the filtrate. Specifically, the content of the recycled isosorbide contained in the filtrate may be 0.2 to 15% by weight, 0.25 to 13% by weight, 0.3 to 10% by weight, 0.35 to 8% by weight, or 0.4 to 7% by weight, based on the total weight of the filtrate. Here, when the content of the recycled isosorbide is within the above range, it may mean that the recovery rate of isosorbide is high.

Specifically, according to the present invention, the recovery rate ($ISB_R$) of isosorbide according to the following Equation 3 may be 80% or more, 82% or more, 84% or more, 86% or more, or 88% or more (e.g., 80 to 99.5%, 82 to 99%, 84 to 98.5%, or 86 to 98%).

$$ISB_R = (ISB_B/ISB_A) \times 100 \qquad \text{[Equation 3]}$$

in Equation 3, $ISB_A$ is the weight of isosorbide fed to the waste copolyester (introduced during the preparation of the waste copolyester), and $ISB_B$ is the weight of isosorbide contained in the filtrate.

The fifth reactant obtained through step (4) may be subjected to a drying process using a vacuum oven or the like, through which recycled bis-2-hydroxyethyl terephthalate can be recovered. In addition, the filtrate obtained through step (4) may be subjected to an additional purification process, through which recycled isosorbide can be recovered.

As described above, various recycled raw materials can be prepared according to the present invention, and the recycled raw materials obtained according to the preparation method of the present invention may be significantly excellent in purity and quality. Therefore, the recycled raw materials obtained according to the present invention can be efficiently used as raw materials for the preparation of recycled polyesters (recycled copolyesters).

Recycled Raw Material Composition

The present invention provides a recycled raw material composition obtained from a waste copolyester. The description of the waste copolyester is the same as described above and, therefore, will be omitted. The recycled raw material composition according to the present invention may be a reactant (product) obtained through the preparation method described above.

Specifically, the recycled raw material composition according to the present invention is obtained by the depolymerization of a waste copolyester, wherein the peak area fraction of bis-2-hydroxyethyl terephthalate is 70% or less, and the peak area fraction of a diol-ester is 10% or more, when analyzed by high-performance liquid chromatography (HPLC).

More specifically, the recycled raw material composition (A) according to the present invention may be one (e.g., fourth reactant) obtained by the depolymerization of a waste copolyester and thin film evaporation. This recycled raw material composition (A) may have a peak area fraction of bis-2-hydroxyethyl terephthalate of 20 to 70%, 25 to 67%, 30 to 65%, or 40 to 50%, and a peak area fraction of a diol-ester (e.g., cyclohexanedimethanol-ester) of 10 to 40%, 11 to 38%, 15 to 35%, or 20 to 30%, when analyzed by high-performance liquid chromatography (HPLC).

Meanwhile, the recycled raw material composition (B) according to the present invention is obtained by the depolymerization of a waste copolyester, wherein the peak area fraction of bis-2-hydroxyethyl terephthalate is 95% or more, and the peak area fraction of a diol-ester is less than 1.5%, when analyzed by high-performance liquid chromatography (HPLC).

More specifically, the recycled raw material composition (B) according to the present invention may be one (e.g., fifth reactant) obtained by the depolymerization of a waste copolyester, thin film evaporation, and recrystallization. This recycled raw material composition (B) may have a peak area fraction of bis-2-hydroxyethyl terephthalate of 95 to 99.5%, 95.5 to 99%, 96 to 98%, or 97 to 98%, and a peak area fraction of a diol-ester (e.g., cyclohexanedimethanol-ester) of 0.2 to 1.4%, 0.3 to 1.3%, 0.4 to 1.2%, or 0.5 to 1.1%, when analyzed by high-performance liquid chromatography (HPLC).

Meanwhile, the diol-ester, identified as a result of the analysis by high-performance liquid chromatography (HPLC), may specifically comprise at least one selected from the group consisting of a cyclohexanedimethanol-ester (CHDM-ester), a tetramethylcyclobutanediol-ester (TMCBD-ester), a neopentylglycol-ester (NPG-ester), and an isosorbide-ester (ISB-ester).

As the recycled raw material compositions (A and B) according to the present invention are analyzed to comprise bis-2-hydroxyethylterephthalate and/or a diol-ester in certain proportions as described above, the present invention can efficiently provide various kinds of recycled raw 1 materials together with recycled bis-2-hydroxyethylterephthalate.

MODE FOR THE INVENTION

Hereinafter, the present invention will be described in more detail with reference to embodiments. However, these examples are provided only for illustration purposes, and the present invention is not limited thereto.

Example 1

A first reactor made of stainless steel (SUS) was charged with 1,000 g of a waste copolyester having Composition 1 shown in Table 1 below, 2,000 g of ethylene glycol, and 5.0 g of zinc acetate anhydride. The temperature inside the reactor was raised to 180° C., and a first depolymerization (first glycolysis reaction) was carried out for 2 hours. As a result, a first-first reactant was obtained.

Subsequently, the first-first reactant was transferred to a second reactor and cooled to 150° C. 2,000 g of ethylene glycol was further added thereto, and a second depolymerization (second glycolysis reaction) was carried out for 2 hours while the reactor temperature was maintained at 150° C. As a result, a first reactant was obtained.

Next, the first reactant was cooled to 120° C. through reduced pressure flash, and 16 g of a filter aid (CELITE™ 545) was added thereto, followed by pressurized filtration to carry out solid-liquid separation.

The liquid reactant obtained by the solid-liquid separation was passed through a column filled with an ion-exchange resin (BC107(H) of Bonlite) to remove ionic impurities to obtain a second reactant comprising crude recycled bis-2-hydroxyethyl terephthalate (crude r-BHET) and unreacted ethylene glycol.

Next, the second reactant was transferred to a 10-liter distillation apparatus, and vacuum distillation was carried out at 130° C. to recover unreacted ethylene glycol. As a result, a second-first reactant from which ethylene glycol had been removed was obtained.

Next, 7.8 g of activated carbon was added to 1,560 g of the second-first reactant. And solid-liquid separation was carried out to remove the residual chromophore, and separation was then carried out with a thin film evaporator (VKL70-4S of VTA). Specifically, the thin film evaporation was carried out at 210° C. and 0.08 Torr to obtain 952 g of a third reactant containing crude r-BHET and 608 g of a fourth reactant containing recycled diol-esters, respectively.

Next, a glass reactor was charged with the third reactant and distilled water equivalent to three times the weight of the third reactant, and it was dissolved at 70° C., which was then cooled to room temperature, crystallized, filtered, and dried in a vacuum oven to obtain a fifth reaction containing recycled bis-2-hydroxyethyl terephthalate (r-BHET) with high purity. In addition, the filtrate obtained through filtration after the cooling and crystallization was recovered as a sixth reactant.

Examples 2 to 4

Each step was carried out through the same procedure as in Example 1, except that a waste copolyester having each of Compositions 2 to 4 in Table 1 below was used.

Example 5

Each step was carried out through the same procedure as in Example 1, except that the thin film evaporation was carried out at 240° C.

Comparative Example 1

Each step was carried out through the same procedure as in Example 1, except that a waste polyester (waste polyester terephthalate (PET)) having Composition 5 in Table 1 below was used.

TABLE 1

| Composition of waste polyester | | | Composition 1 (Exs. 1 and 5) | Composition 2 (Ex. 2) | Composition 3 (Ex. 3) | Composition 4 (Ex. 4) | Composition 5 (C. Ex. 1) |
|---|---|---|---|---|---|---|---|
| Acid | TPA | mole % | 100.0 | 100.0 | 100.0 | 100.0 | 100 |
| Alcohol | CHDM | | 32.0 | 67.0 | 14.0 | 45.0 | 0 |
| | MEG | | 66.0 | 33.0 | 80.0 | 21.0 | 100 |
| | DEG | | 2.0 | 0.0 | 1.0 | 1.0 | 0 |
| | ISB | | 0.0 | 0.0 | 5.0 | 33.0 | 0 |
| Acid | TPA | wt % | 65.1 | 58.7 | 68.0 | 56.7 | 73.0 |
| Alcohol | CHDM | | 18.1 | 34.1 | 8.3 | 22.1 | 0.0 |
| | MEG | | 16.0 | 7.2 | 20.3 | 4.4 | 27.0 |
| | DEG | | 0.8 | 0.0 | 0.4 | 0.4 | 0.0 |
| | ISB | | 0.0 | 0.0 | 3.0 | 16.4 | 0.0 |

TPA: terephthalic acid
CHDM: cyclohexanedimethanol
MEG: monoethylene glycol
DEG: diethylene glycol
ISB: isosorbide

Test Example 1

The reactant obtained in each step was analyzed by high-performance liquid chromatography (HPLC) under the following conditions. The results are shown in Tables 2 to 4 below.

Pretreatment: About 0.01 g of each reactant was diluted in about 20 ml of methanol and then analyzed by high-performance liquid chromatography (HPLC).
HPLC analysis equipment (model): Waters e2695
Column: C18 (4.6×250 mm), 5 μm
UV detector: 242 nm
Injection volume: 10 μl
Eluent (gradient): A—$H_2O+H_3PO_4$, B—Acetonitrile Thereafter, the peak area fractions (area %) of the respective components among the total peak area of HPLC were obtained.

Test Example 2

The recovery concentration index (RCI) was calculated according to the following Equation 1. The results are shown in Tables 2 to 4 below. Here, CHDM-ester-1, Dimer-2, Dimer-3, and Trimer-2 were taken as the diol-ester (cyclohexanedimethanol-ester) components in Tables 2 to 4 below.

$$RCI = CE_2/(CE_1 + CE_2) \qquad \text{[Equation 1]}$$

In Equation 1, $CE_1$ is the peak area fraction of the identified diol-ester when the third reactant is analyzed by high-performance liquid chromatography (HPLC), and $CE_2$ is the peak area fraction of the identified diol-ester when the fourth reactant is analyzed by high-performance liquid chromatography (HPLC).

Test Example 3

The filtrate recovered as the sixth reactant was analyzed by gas chromatography (GC) under the following conditions. The results are shown in Tables 2 to 4 below.

Pretreatment: About 0.1 g of the filtrate was diluted in about 10 ml of $CHCl_3$, treated with a filter of 0.45 μm, and then analyzed by gas chromatography (GC).

GC analysis equipment (model): Agilent 7890B
Column: DB-624 (30 m×0.25 mm×1.4 μm)
Oven Temp.: 60° C. (2 min.)–10° C./min.-200° C. (0 min.)-20° C./min.-260° C. (5 min.)
Injector temp.: 250° C.
Detector temp.: 250° C.
Flow: 1.5 mL/min (N2), split ratio: 1/50

TABLE 2

| | | Ex. 1 | | | Ex. 2 | | |
|---|---|---|---|---|---|---|---|
| | | Third reactant | Fourth reactant | Fifth reactant | Third reactant | Fourth reactant | Fifth reactant |
| HPLC (Area %) | MHET | 2.19 | 0.77 | 1.51 | 1.98 | 0.69 | 1.19 |
| | BHET | 95.20 | 64.76 | 97.00 | 94.14 | 53.48 | 97.78 |
| | DEG-ester-1 | 0.36 | 0.89 | 0.21 | 0.36 | 0.65 | 0.16 |
| | DEG-ester-2 | 0.01 | 0.05 | 0.00 | 0.01 | 0.04 | 0.00 |
| | Dimer-1 | 0.08 | 11.06 | 0.17 | 0.14 | 9.78 | 0.06 |
| | CHDM-ester-1 | 1.36 | 14.49 | 0.71 | 2.81 | 24.67 | 0.62 |
| | Trimer-1 | 0.07 | 0.83 | 0.06 | 0.01 | 0.72 | 0.03 |
| | Dimer-2 (cis-CHDM unit 1) | 0.01 | 1.36 | 0.02 | 0.01 | 2.11 | 0.00 |
| | Dimer-3 (trans-CHDM unit 1) | 0.01 | 3.84 | 0.05 | 0.03 | 5.39 | 0.01 |
| | BHCMT | 0.00 | 0.62 | 0.02 | 0.01 | 1.56 | 0.00 |
| | Trimer-2 (CHDM unit-1) | 0.10 | 0.40 | 0.04 | 0.30 | 0.14 | 0.01 |
| | Others | 0.6 | 0.9 | 0.2 | 0.2 | 0.8 | 0.1 |
| | CHDM-ester total | 1.5 | 20.1 | 0.8 | 3.2 | 32.3 | 0.6 |
| | RCI (CHDM-ester) | | 0.931 | | | 0.911 | |
| GC (wt %) | Content of ISB in the filtrate (wt %) | | N.D. | | | N.D. | |
| | Recovery rate of ISB (%) | | | | | | |

MHET: monohydroxyethyl terephthalate
BHET: bis-2-hydroxyethyl terephthalate
DEG-ester-1: 2-hydroxyethyl[2-(2-hydroxyethoxy)ethyl] terephthalate
DEG-ester-2: bis[2-(2-hydroxyethoxy)ethyl]benzene-1,4-dicarboxylate
Dimer-1: BHET dimer
Trimer-1: BHET trimer
CHDM-ester-1: 1-(2-hydroxyethyl) 4-[[4-(hydroxymethyl)cyclohexyl]methyl] terephthalate
Dimer-2: 1,1'-[1,4-cyclohexanediylbis(methylene)] 4,4'-bis(2-hydroxyethyl) terephthalate (cis form)
Dimer-3: 1,1'-[1,4-cyclohexanediylbis(methylene)] 4,4'-bis(2-hydroxyethyl) terephthalate (trans form)
BHCMT: 1,4-bis [[4-(hydroxymethyl)cyclohexyl]methyl] terephthalate
Trimer-2: 1,4-benzenedicarboxylic acid, 1-[2-[[4-[(2-hydroxyethoxy)carbonyl]benzoyl]oxy]ethyl]-4-[2-[[4-[([(hydroxymethyl)cyclohexyl]methoxy)carbonyl]benzoyl]oxy]ethyl]ester
CHDM-ester total = CHDM-ester-1 + Dimer-2 + Dimer-3 + Trimer-2
ISB: isosorbide
N.D.: not detected

TABLE 3

| | | Ex. 3 | | | Ex. 4 | | | Ex. 5 | | |
|---|---|---|---|---|---|---|---|---|---|---|
| | | Third reactant | Fourth reactant | Fifth reactant | Third reactant | Fourth reactant | Fifth reactant | Third reactant | Fourth reactant | Fifth reactant |
| HPLC (Area %) | MHET | 1.34 | 0.33 | 1.04 | 3.25 | 0.36 | 0.93 | 3.40 | 0.20 | 1.92 |
| | BHET | 93.50 | 56.54 | 97.78 | 92.55 | 42.17 | 97.05 | 85.30 | 66.20 | 97.22 |
| | DEG-ester-1 | 0.64 | 1.52 | 0.21 | 0.47 | 1.37 | 0.23 | 0.56 | 0.89 | 0.21 |
| | DEG-ester-2 | 0.02 | 0.09 | 0.00 | 0.01 | 0.06 | 0.00 | 0.04 | 0.05 | 0.01 |
| | Dimer-1 | 2.02 | 26.18 | 0.29 | 0.62 | 13.26 | 0.28 | 0.56 | 22.10 | 0.15 |
| | CHDM-ester-1 | 1.27 | 7.48 | 0.50 | 1.39 | 27.61 | 0.94 | 8.56 | 6.42 | 0.12 |

TABLE 3-continued

|  |  | Ex. 3 | | | Ex. 4 | | | Ex. 5 | | |
| --- | --- | --- | --- | --- | --- | --- | --- | --- | --- | --- |
|  |  | Third reactant | Fourth reactant | Fifth reactant | Third reactant | Fourth reactant | Fifth reactant | Third reactant | Fourth reactant | Fifth reactant |
|  | Trimer-1 | 0.17 | 2.17 | 0.04 | 0.00 | 1.07 | 0.04 | 0.10 | 0.67 | 0.02 |
|  | Dimer-2 (cis-CHDM unit 1) | 0.07 | 0.92 | 0.01 | 0.03 | 2.51 | 0.03 | 0.13 | 1.22 | 0.01 |
|  | Dimer-3 (trans-CHDM unit 1) | 0.21 | 2.92 | 0.01 | 0.12 | 7.76 | 0.12 | 0.14 | 1.32 | 0.02 |
|  | BHCMT | 0.00 | 0.17 | 0.00 | 0.43 | 2.02 | 0.03 | 0.32 | 0.54 | 0.02 |
|  | Trimer-2 (CHDM unit-1) | 0.53 | 0.30 | 0.00 | 0.02 | 0.27 | 0.04 | 0.44 | 0.22 | 0.00 |
|  | Others | 0.2 | 1.4 | 0.1 | 1.1 | 1.5 | 0.3 | 0.5 | 0.2 | 0.3 |
|  | CHDM-ester total | 2.1 | 11.6 | 0.5 | 1.6 | 38.2 | 1.1 | 9.3 | 9.2 | 0.2 |
|  | RCI (CHDM-ester) |  | 0.848 |  |  | 0.961 |  |  | 0.498 |  |
| GC (wt %) | Content of ISB in the filtrate (wt %) |  | 0.46 |  |  | 5.23 |  |  | N.D. |  |
|  | Recovery rate of ISB (%) |  | 89.7 |  |  | 95.1 |  |  |  |  |

MHET: monohydroxyethyl terephthalate
BHET: bis-2-hydroxyethyl terephthalate
DEG-ester-1: 2-hydroxyethyl[2-(2-hydroxyethoxy)ethyl] terephthalate
DEG-ester-2: bis[2-(2-hydroxyethoxy)ethyl]benzene-1,4-dicarboxylate
Dimer-1: BHET dimer
Trimer-1: BHET trimer
CHDM-ester-1: 1-(2-hydroxyethyl) 4-[[4-(hydroxymethyl)cyclohexyl]methyl] terephthalate
Dimer-2: 1,1'-[1,4-cyclohexanediylbis(methylene)] 4,4'-bis(2-hydroxyethyl) terephthalate (cis form)
Dimer-3: 1,1'-[1,4-cyclohexanediylbis(methylene)] 4,4'-bis(2-hydroxyethyl) terephthalate (trans form)
BHCMT: 1,4-bis[[4-(hydroxymethyl)cyclohexyl]methyl] terephthalate
Trimer-2: 1,4-benzenedicarboxylic acid, 1-[2-[4-[(2-hydroxyethoxy)carbonyl]benzoyl]oxy]ethyl]-4-[2-[[4-[([(hydroxymethyl)cyclohexyl]methoxy)carbonyl]benzoyl]oxy]ethyl] ester
CHDM-ester total = CHDM-ester-1 + Dimer-2 + Dimer-3 + Trimer-2
ISB: isosorbide
N.D.: not detected

TABLE 4

|  |  | C. Ex. 1 | | |
| --- | --- | --- | --- | --- |
|  |  | Third reactant | Fourth reactant | Fifth reactant |
| HPLC (Area %) | MHET | 2.18 | 0.74 | 1.35 |
|  | BHET | 96.57 | 61.45 | 98.15 |
|  | DEG-ester-1 | 0.79 | 1.99 | 0.29 |
|  | DEG-ester-2 | 0.01 | 0.07 | 0.00 |
|  | Dimer-1 | 0.18 | 29.70 | 0.11 |
|  | CHDM-ester-1 | 0.00 | 0.00 | 0.00 |
|  | Trimer-1 | 0.01 | 1.24 | 0.01 |
|  | Dimer-2 (cis-CHDM unit 1) | 0.00 | 0.00 | 0.00 |
|  | Dimer-3 (trans-CHDM unit 1) | 0.00 | 0.00 | 0.00 |
|  | BHCMT | 0.00 | 0.00 | 0.00 |
|  | Trimer-2 (CHDM unit-1) | 0.00 | 0.00 | 0.00 |
|  | Others | 0.3 | 4.8 | 0.1 |
|  | CHDM-ester total | 0.0 | 0.0 | 0.0 |
| RCI (CHDM-ester) |  |  | — |  |
| GC (wt %) | Content of ISB in the filtrate (wt %) |  | N.D. |  |
|  | Recovery rate of ISB (%) |  |  |  |

MHET: monohydroxyethyl terephthalate
BHET: bis-2-hydroxyethyl terephthalate
DEG-ester-1: 2-hydroxyethyl[2-(2-hydroxyethoxy)ethyl] terephthalate
DEG-ester-2: bis[2-(2-hydroxyethoxy)ethyl]benzene-1,4-dicarboxylate
Dimer-1: BHET dimer
Trimer-1: BHET trimer
CHDM-ester-1: 1-(2-hydroxyethyl) 4-[[4- (hydroxymethyl)cyclohexyl]methyl] terephthalate
Dimer-2: 1,1'-[1,4-cyclohexanediylbis(methylene)] 4,4'-bis(2-hydroxyethyl) terephthalate (cis form)
Dimer-3: 1,1'-[1,4-cyclohexanediylbis(methylene)] 4,4'-bis(2-hydroxyethyl) terephthalate (trans form)
BHCMT: 1,4-bis[[4-(hydroxymethyl)cyclohexyl]methyl] terephthalate
Trimer-2: 1,4-benzenedicarboxylic acid, 1-[2-[4-[(2-hydroxyethoxy)carbonyl]benzoyl]oxy]ethyl]-4-[2-[[4-[([(hydroxymethyl)cyclohexyl]methoxy)carbonyl]benzoyl]oxy]ethyl] ester
CHDM-ester total = CHDM-ester-1 + Dimer-2 + Dimer-3 + Trimer-2
ISB: isosorbide
N.D.: not detected Referring to Tables 2 to 4 above, when recycled raw materials (Examples 1 to 5) were prepared through the preparation method of the present invention, various recycled raw materials (r-BHET, r-CHDM, and r-ISB) could be prepared at high yields. In particular, since the recovery concentration index (RCI) of the CHDM-ester was 0.5 or more, it was possible to prepare (recover) r-CHDM, r-ISB, and the like, which are comonomers that have been difficult to recycle in the past.

The invention claimed is:

1. A method for preparing a recycled raw material, which comprises:
   (1) depolymerizing a waste copolyester to obtain a first reactant;
   (2) removing impurities present in the first reactant to obtain a second reactant;
   (3) distilling the second reactant to obtain a third reactant comprising crude recycled bis-2-hydroxyethyl terephthalate and a fourth reactant comprising a recycled diol-ester; and
   (4) mixing the third reactant with an aqueous solvent and recrystallizing it to obtain a fifth reactant comprising recycled bis-2-hydroxyethyl terephthalate and a filtrate.

2. The method for preparing a recycled raw material of claim 1, wherein step (1) comprises (1-1) first depolymerizing the waste copolyester to obtain a first-first reactant; and (1-2) second depolymerizing the first-first reactant to obtain the first reactant.

3. The method for preparing a recycled raw material of claim 2, wherein the first depolymerization in step (1-1) is carried out at 180 to 200° C.

4. The method for preparing a recycled raw material of claim 2, wherein the second depolymerization in step (1-2) is carried out at 150 to 170° C.

5. The method for preparing a recycled raw material of claim 1, wherein step (3) comprises (3-1) first distilling the second reactant to obtain a second-first reactant; and (3-2) second distilling the second-first reactant to obtain the third reactant and the fourth reactant.

6. The method for preparing a recycled raw material of claim 5, wherein the first distillation in step (3-1) is carried out as vacuum distillation at 150° C. or lower.

7. The method for preparing a recycled raw material of claim 5, wherein the second distillation in step (3-2) is carried out as thin film evaporation at 180 to 235° C.

8. The method for preparing a recycled raw material of claim 1, wherein the fourth reactant of step (3) comprises at least one selected from the group consisting of a recycled cyclohexanedimethanol-ester and recycled cyclohexanedimethanol.

9. The method for preparing a recycled raw material of claim 1, wherein the third reactant of step (3) has a peak area fraction of bis-2-hydroxyethyl terephthalate of 90% or more and a peak area fraction of a diol-ester of 4% or less, wherein the peak area fractions are analyzed by high-performance liquid chromatography (HPLC).

10. The method for preparing a recycled raw material of claim 1, wherein the fourth reactant of step (3) has a peak area fraction of bis-2-hydroxyethyl terephthalate of 70% or less and a peak area fraction of a diol-ester of 10% or more, wherein the peak areas are analyzed by high-performance liquid chromatography (HPLC).

11. The method for preparing a recycled raw material of claim 1, wherein the recovery concentration index (RCI) according to the following Equation 1 is 0.5 to 0.99:

$$RCI = CE_2/(CE_1 + CE_2) \qquad \text{[Equation 1]}$$

in Equation 1, $CE_1$ is the peak area fraction of the identified diol-ester of the third reactant measured by high-performance liquid chromatography (HPLC), and $CE_2$ is the peak area fraction of the identified diol-ester of the fourth reactant analyzed by high-performance liquid chromatography (HPLC).

12. The method for preparing a recycled raw material of claim 1, wherein step (4) comprises (4-1) mixing the third reactant with the aqueous solvent to obtain an aqueous solution; and (4-2) cooling and crystallizing the aqueous solution to give a crystallization product and subjecting the crystallization product to solid-liquid separation to obtain the fifth reactant and the filtrate.

13. The method for preparing a recycled raw material of claim 1, wherein the fifth reactant of step (4) has a peak area fraction of bis-2-hydroxyethyl terephthalate of 95% or more and a peak area fraction of a diol-ester of less than 1.5%, wherein the peak areas are analyzed by high-performance liquid chromatography (HPLC).

14. The method for preparing a recycled raw material of claim 1, wherein the total peak area fraction of a diol-ester of the fourth reactant of step (3) and the fifth reactant of step (4) is 0.1 to 70%, wherein the peak area fractions are analyzed by high-performance liquid chromatography (HPLC).

15. The method for preparing a recycled raw material of claim 1, wherein the filtrate of step (4) comprises recycled isosorbide in an amount of 0.1 to 30% by weight based on the total weight of the filtrate.

16. A recycled raw material composition, which is obtained by the depolymerization of a waste copolyester of claim 1, comprising bis-2-hydroxyethyl terephthalate and a diol-ester, wherein a peak area fraction of the bis-2-hydroxyethyl terephthalate is 70% or less, and a peak area fraction of the diol-ester is 10% or more, wherein the peak area fractions are analyzed by high-performance liquid chromatography (HPLC).

17. The recycled raw material composition of claim 16, wherein the diol-ester comprises one or more selected from the group consisting of a cyclohexanedimethanol-ester, a tetramethylcyclobutanediol-ester, a neopentylglycol-ester, and an isosorbide-ester.

18. A recycled raw material composition, which is obtained by the depolymerization of a waste copolyester of claim 1, comprising bis-2-hydroxyethyl terephthalate and a diol-ester, wherein a peak area fraction of the bis-2-hydroxyethyl terephthalate is 95% or more, and a peak area fraction of the diol-ester is less than 1.5%, wherein the peak area fractions are analyzed by high-performance liquid chromatography.

19. The recycled raw material composition of claim 18, wherein the diol-ester comprises one or more selected from the group consisting of a cyclohexanedimethanol-ester, a tetramethylcyclobutanediol-ester, a neopentylglycol-ester, and an isosorbide-ester.

* * * * *